(12) United States Patent
Higuita-Castro et al.

(10) Patent No.: US 12,221,471 B2
(45) Date of Patent: Feb. 11, 2025

(54) NANOCARRIERS FOR LUNG INFLAMMATION THERAPY

(71) Applicant: Ohio State Innovation Foundation, Columbus, OH (US)

(72) Inventors: Natalia Higuita-Castro, Columbus, OH (US); Daniel Gallego-Perez, Columbus, OH (US); Samir Ghadiali, Upper Arlington, OH (US); Joshua Englert, Powell, OH (US); Chandan Sen, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 632 days.

(21) Appl. No.: 17/284,286

(22) PCT Filed: Oct. 18, 2019

(86) PCT No.: PCT/US2019/056997
§ 371 (c)(1),
(2) Date: Apr. 9, 2021

(87) PCT Pub. No.: WO2020/081974
PCT Pub. Date: Apr. 23, 2020

(65) Prior Publication Data
US 2021/0332106 A1 Oct. 28, 2021

Related U.S. Application Data

(60) Provisional application No. 62/747,987, filed on Oct. 19, 2018.

(51) Int. Cl.
| | |
|---|---|
| *C07K 14/785* | (2006.01) |
| *A61K 9/51* | (2006.01) |
| *A61K 38/17* | (2006.01) |
| *A61P 11/00* | (2006.01) |
| *C12N 15/88* | (2006.01) |

(52) U.S. Cl.
CPC .............. *C07K 14/785* (2013.01); *A61K 9/51* (2013.01); *A61K 38/17* (2013.01); *A61P 11/00* (2018.01); *C12N 15/88* (2013.01)

(58) Field of Classification Search
CPC ............ C07K 14/785; C07K 14/70596; C07K 2319/03; A61K 9/51; A61K 38/17; A61K 9/5176; A61K 38/1774; A61P 11/00; C12N 15/88; C12N 15/62
See application file for complete search history.

(56) References Cited

U.S. PATENT DOCUMENTS

2016/0095864 A1 4/2016 Park et al.
2018/0215758 A1 8/2018 Accetta

FOREIGN PATENT DOCUMENTS

| CN | 1838964 A | 9/2006 |
|---|---|---|
| WO | 2014072468 A1 | 5/2014 |
| WO | 2015016761 | 2/2015 |
| WO | 2017075708 A1 | 5/2017 |
| WO | 2018015535 | 1/2018 |

OTHER PUBLICATIONS

Margaret Alexander, Exosome-delivered microRNAs modulate the inflammatory response to endotoxin, 2015, pp. 1-16.*
Herold, Susanne, "Acute lung injury: how macrophages orchestrate resolution of inflammation and tissue repair", Frontiers in Immunology, vol. 2, Article 65, pp. 1-13, Nov. 24, 2011.
Chinese Search Report in co-pending, related Chinese Application No. CN 2019800734398, mailed Jul. 27, 2022.
International Search Report issued for PCT/US2019/056997, mailed Mar. 4, 2020.
Horie Shahd et al: "Cell therapy in acute 1-11 respiratory distress syndrome", Journal of Thoracic Disease, vol. 10, No. 9, Sep. 1, 2018 (Sep. 1, 2018), pp. 5607-5620, XP055817419, China ISSN: 2072-1439, DOI: 10.21037/jtd.2018.08.28 Retrieved from the Internet: URL:https://www.ncbi.nlm.nih.gov/pmc/articles/PMC6196176/pdf/jtd-10-09-5607.pdf>.
Lu Mei et al: "Functionalized extracellular vesicles as advanced therapeutic nanodelivery systems", European Journal of Pharmaceutical Sciences, Elsevier Amsterdam, NL, vol. 121, May 4, 2018 (May 4, 2018), 34-46, XP085413298, ISSN: 0928-0987, DOI: 10.1016/J.EJPS.2018.05.001.
Pablo Garc & #237A—Manrique et al: "Therapeutic biomaterials based on extracellular vesicles: classification of bio-engineering and mimetic preparation routes", Journal of Extracellular Vesicles, vol. 7, No. 1, Jan. 17, 2018 (Jan. 17, 2018), p. 1422676, XP055541251, DOI: 10.1080/20013078.2017.1422676.
Extended European Search Report for Application No. 19873828 mailed Jul. 19, 2022.

* cited by examiner

*Primary Examiner* — Jeanette M Lieb
*Assistant Examiner* — Erinne R Dabkowski
(74) *Attorney, Agent, or Firm* — Thomas | Horstemeyer, LLP

(57) ABSTRACT

Disclosed are lung-targeted extracellular vesicles (EVs) loaded with an anti-inflammatory cargo, as well as compositions, systems, and methods for making same. The disclosed EVs can contain a lung targeted ligand, such as a fusion protein containing a lung targeting moiety. Also disclosed is a composition comprising an EV containing the disclosed fusion protein. In some embodiments, the EV is loaded with an anti-inflammatory cargo. Also disclosed is an EV-producing cell engineered to produce the disclosed EVs. Also disclosed is a method for making the disclosed EVs that involves culturing the disclosed EV-producing cells under conditions suitable to produce EVs.

4 Claims, 11 Drawing Sheets
Specification includes a Sequence Listing.

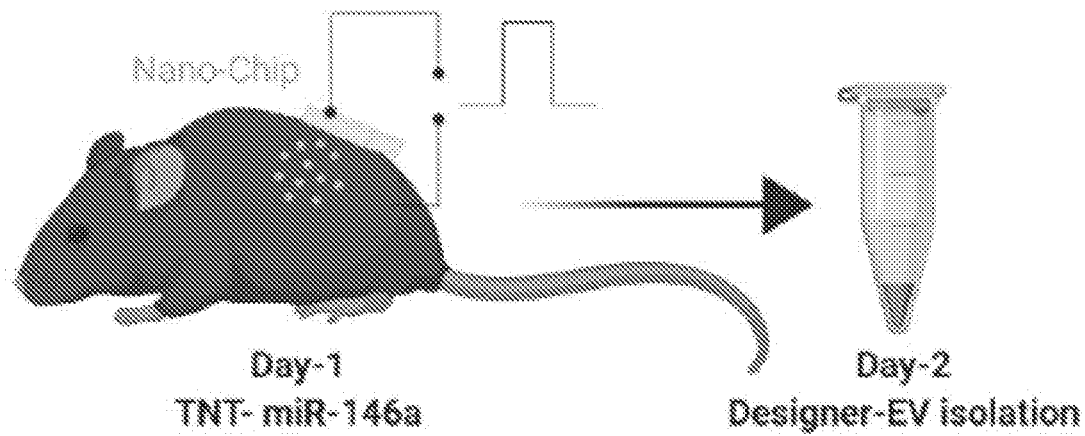
FIG. 4A
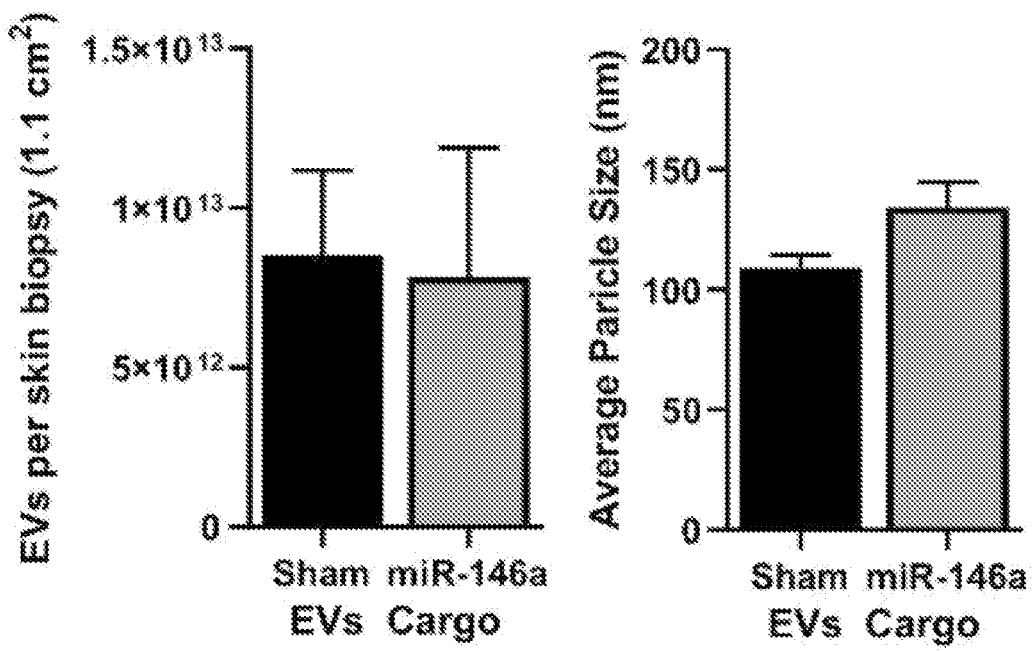
FIG. 4B                    FIG. 4C

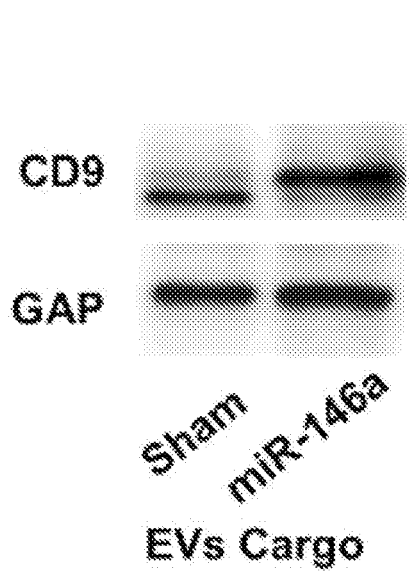
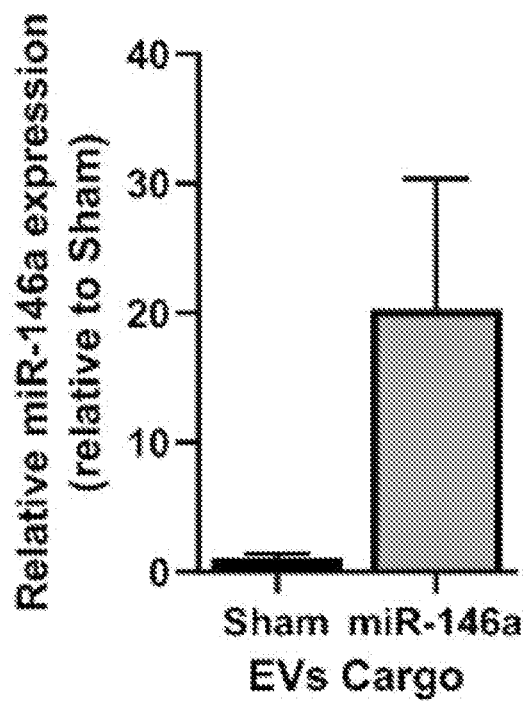
FIG. 4D
FIG. 4E
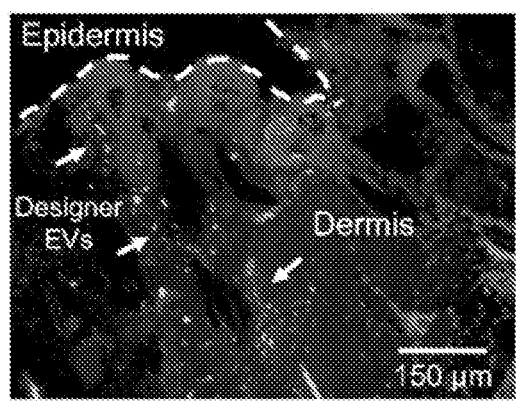
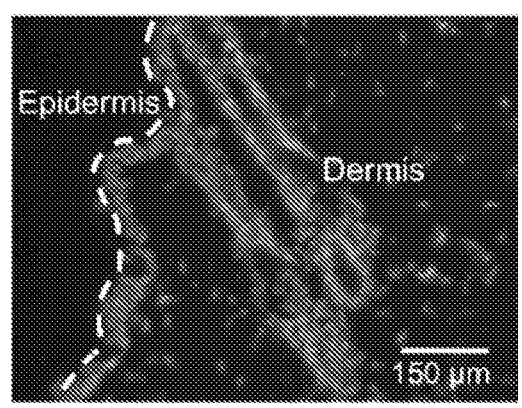
FIG. 4F
FIG. 4G

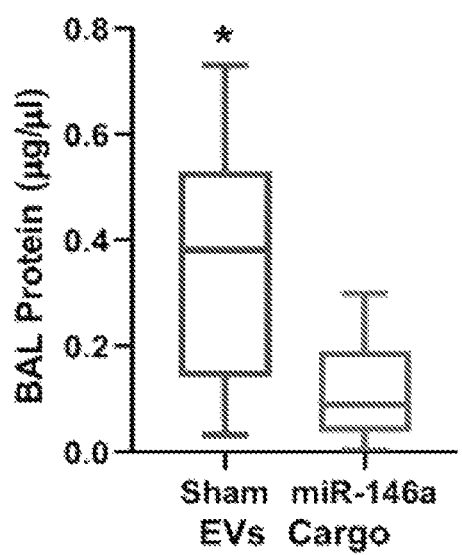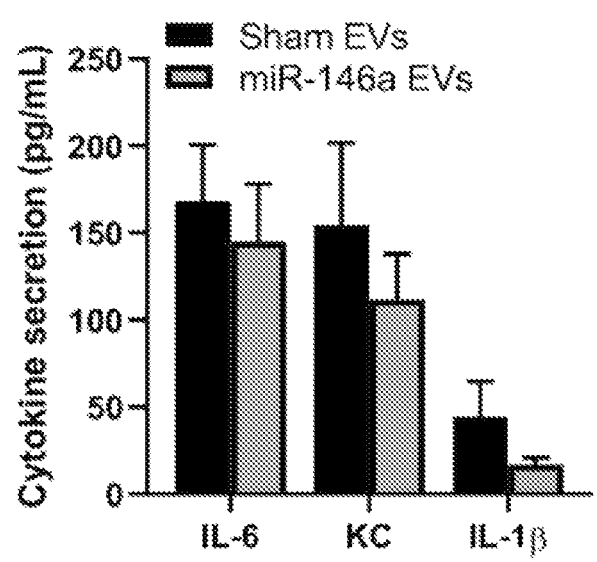
FIG. 5E                                    FIG. 5F

SEQUENCE LISTING

```
<160> NUMBER OF SEQ ID NOS: 3

<210> SEQ ID NO 1
<211> LENGTH: 199
<212> TYPE: PRT
<213> ORGANISM: Artificial Sequence
<220> FEATURE:
<223> OTHER INFORMATION: Synthetic Construct

<400> SEQUENCE: 1

Met Trp Leu Cys Pro Leu Ala Leu Asn Leu Ile Leu Met Ala Ala Ser
1               5                   10                  15

Gly Ala Val Cys Glu Val Lys Asp Val Cys Val Gly Thr Pro Gly Ile
            20                  25                  30

Pro Gly Glu Cys Gly Glu Lys Gly Glu Pro Gly Glu Arg Gly Pro Pro
        35                  40                  45

Gly Leu Pro Ala His Leu Asp Glu Glu Leu Gln Ala Thr Leu His Asp
    50                  55                  60

Phe Arg His Gln Ile Leu Gln Thr Arg Gly Ala Leu Ser Leu Gln Gly
65                  70                  75                  80

Ser Ile Met Thr Val Gly Glu Lys Val Phe Ser Ser Asn Gly Gln Ser
                85                  90                  95

Ile Thr Phe Asp Ala Ile Gln Glu Ala Cys Ala Arg Ala Gly Gly Arg
            100                 105                 110

Ile Ala Val Pro Arg Asn Pro Glu Glu Asn Glu Ala Ile Ala Ser Phe
        115                 120                 125

Val Lys Lys Tyr Asn Thr Tyr Ala Tyr Val Gly Leu Thr Glu Gly Pro
    130                 135                 140

Ser Pro Gly Asp Phe Arg Tyr Ser Asp Gly Thr Pro Val Asn Tyr Thr
145                 150                 155                 160
```

Asn Trp Tyr Arg Gly Glu Pro Ala Gly Arg Gly Lys Glu Gln Cys Val
            165                 170                 175

Glu Met Tyr Thr Asp Gly Gln Trp Asn Asp Arg Asn Cys Leu Tyr Ser
            180                 185                 190

Arg Leu Thr Ile Cys Glu Phe
            195

<210> SEQ ID NO 2
<211> LENGTH: 248
<212> TYPE: PRT
<213> ORGANISM: Artificial Sequence
<220> FEATURE:
<223> OTHER INFORMATION: Synthetic Construct

<400> SEQUENCE: 2

Met Trp Leu Cys Pro Leu Ala Leu Thr Leu Ile Leu Met Ala Ala Ser
1               5                   10                  15

Gly Ala Ala Cys Glu Val Lys Asp Val Cys Val Gly Ser Pro Gly Ile
            20                  25                  30

Pro Gly Thr Pro Gly Ser His Gly Leu Pro Gly Arg Asp Gly Arg Asp
        35                  40                  45

Gly Val Lys Gly Asp Pro Gly Pro Pro Gly Pro Met Gly Pro Pro Gly
    50                  55                  60

Glu Thr Pro Cys Pro Pro Gly Asn Asn Gly Leu Pro Gly Ala Pro Gly
65                  70                  75                  80

Val Pro Gly Glu Arg Gly Glu Lys Gly Glu Ala Gly Glu Arg Gly Pro
                85                  90                  95

Pro Gly Leu Pro Ala His Leu Asp Glu Glu Leu Gln Ala Thr Leu His
            100                 105                 110

Asp Phe Arg His Gln Ile Leu Gln Thr Arg Gly Ala Leu Ser Leu Gln
        115                 120                 125

Gly Ser Ile Met Thr Val Gly Glu Lys Val Phe Ser Ser Asn Gly Gln
    130                 135                 140

Ser Ile Thr Phe Asp Ala Ile Gln Glu Ala Cys Ala Arg Ala Gly Gly
145                 150                 155                 160

Arg Ile Ala Val Pro Arg Asn Pro Glu Glu Asn Glu Ala Ile Ala Ser
                165                 170                 175

Phe Val Lys Lys Tyr Asn Thr Tyr Ala Tyr Val Gly Leu Thr Glu Gly
            180                 185                 190

Pro Ser Pro Gly Asp Phe Arg Tyr Ser Asp Gly Thr Pro Val Asn Tyr
        195                 200                 205

Thr Asn Trp Tyr Arg Gly Glu Pro Ala Gly Arg Gly Lys Glu Gln Cys
    210                 215                 220

Val Glu Met Tyr Thr Asp Gly Gln Trp Asn Asp Arg Asn Cys Leu Tyr
225                 230                 235                 240

Ser Arg Leu Thr Ile Cys Glu Phe
                245

<210> SEQ ID NO 3
<211> LENGTH: 269
<212> TYPE: PRT
<213> ORGANISM: Artificial Sequence
<220> FEATURE:
<223> OTHER INFORMATION: Synthetic Construct

<400> SEQUENCE: 3

Met Glu Arg Leu Val Ile Arg Met Pro Phe Cys His Leu Ser Thr Tyr

-continued

```
1               5                    10                   15

Ser Leu Val Trp Val Met Ala Ala Val Val Leu Cys Thr Ala Gln Val
            20                  25                  30

Gln Val Val Thr Gln Asp Glu Arg Glu Gln Leu Tyr Thr Pro Ala Ser
            35                  40                  45

Leu Lys Cys Ser Leu Gln Asn Ala Gln Glu Ala Leu Ile Val Thr Trp
        50                  55                  60

Gln Lys Lys Lys Ala Val Ser Pro Glu Asn Met Val Thr Phe Ser Glu
65                      70                  75                  80

Asn His Gly Val Val Ile Gln Pro Ala Tyr Lys Asp Lys Ile Asn Ile
                    85                  90                  95

Thr Gln Leu Gly Leu Gln Asn Ser Thr Ile Thr Phe Trp Asn Ile Thr
                100                 105                 110

Leu Glu Asp Glu Gly Cys Tyr Met Cys Leu Phe Asn Thr Phe Gly Phe
            115                 120                 125

Gly Lys Ile Ser Gly Thr Ala Cys Leu Thr Val Tyr Val Gln Pro Ile
        130                 135                 140

Val Ser Leu His Tyr Lys Phe Ser Glu Asp His Leu Asn Ile Thr Cys
145                     150                 155                 160

Ser Ala Thr Ala Arg Pro Ala Pro Met Val Phe Trp Lys Val Pro Arg
                165                 170                 175

Ser Gly Ile Glu Asn Ser Thr Val Thr Leu Ser His Pro Asn Gly Thr
            180                 185                 190

Thr Ser Val Thr Ser Ile Leu His Ile Lys Asp Pro Lys Asn Gln Val
        195                 200                 205

Gly Lys Glu Val Ile Cys Gln Val Leu His Leu Gly Thr Val Thr Asp
    210                 215                 220

Phe Lys Gln Thr Val Asn Lys Gly Tyr Trp Phe Ser Val Pro Leu Leu
225                 230                 235                 240

Leu Ser Ile Val Ser Leu Val Ile Leu Leu Val Leu Ile Ser Ile Leu
                245                 250                 255

Leu Tyr Trp Lys Arg His Arg Asn Gln Asp Arg Glu Pro
            260                 265
```

NANOCARRIERS FOR LUNG INFLAMMATION THERAPY

CROSS-REFERENCE TO RELATED APPLICATIONS

This application is a National Stage of International Application No. PCT/US2019/056997, filed Oct. 18, 2019, which claims benefit of U.S. Provisional Application No. 62/747,987, filed Oct. 19, 2018, which is hereby incorporated herein by reference in its entirety.

SEQUENCE LISTING

This application contains a sequence listing filed in electronic form as an ASCII.txt file entitled "321501_2340_Sequence_Listing_ST25" created on Oct. 18, 2019. The content of the sequence listing is incorporated herein in its entirety.

BACKGROUND

Acute Respiratory Distress Syndrome (ARDS) is characterized by severe hypoxemia, diffuse bilateral pulmonary infiltrates, and decreased pulmonary compliance. Currently there are no approved treatments for ARDS.

SUMMARY

Disclosed herein is a nanocarrier system to effectively target lung cells loaded with anti-inflammatory cargo to modulate lung inflammation during ARDS. These nanocarriers can be obtained after transfection of cells in vitro or tissues in vivo using diverse transfection techniques (e.g. bulk electroporation, nanoelectroporation, tissue nanotransfection, viral transfection). The disclosed nanocarriers are custom-made extracellular vesicles (EVs) loaded with anti-inflammatory cargo, such as micro-RNA 146a, and are functionalized for targeted delivery via decoration with ligands for specific receptors in the lung microenvironment.

As shown in FIG. 1, loading EVs with anti-inflammatory cargo, and/or decoration with cell-targeting ligands, can be achieved by transfecting, for example, plasmid DNA encoding for the specific cargo or ligand. The cargo could be varied depending on the inflammatory pathway that needs to be regulated, and the surface decoration can be varied depending on the target cell type.

For example, type II pneumocytes and lung macrophages can be targeted using plasmid genes that can encode for surfactant protein-A (SPA) and membrane glycoprotein CD200, respectively. EVs functionalized with SPA interact with receptor P63/CKAP4 on type II cells, while EVs functionalized with CD200 preferentially interact with the CD200R receptor in alveolar macrophages.

The EV can be functionalized with SDF1 which will interact with the receptor CXCR7 in the lung vasculature. This can be valuable, for example, when the EVs are delivered by intravascular methods.

As shown in FIG. 2, surface-decorated EVs can also be loaded with anti-inflammatory cargo that are membrane-permeable pharmacological compounds (e.g., Y-27632 Rho-inhibitor, Calbiochem) that can diffuse into the EVs via a concentration gradient.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 3A and 3B shows designer EVs loaded with miR-146a isolated 24 hours after nanotransfection of primary mouse embryonic fibroblasts (PMEFs), with a particle size in the range of 200 nm and EV concertation in the range of billions of particles per mL. FIG. 3C shows qRT-PCR characterization of miR-146A loaded designer EVs obtained from mouse dendritic cells 48 hours after nanotransfection with plasmids encoding for miR-146A and a sham/control plasmid (*p-value=0.041). FIG. 3D shows relative miR-146A expression in A549 lung epithelial cells and differentiated THP-1 monocytes treated with these miR-146A or sham designer EVs (*p-value<0.001). FIG. 3E shows C57BL/6 mouse primary alveolar epithelial cells after 48 hours of treatment with fluorescently labeled miR-146a designer EVs derived from PMEFs, where white arrows highlights EV uptake.

FIGS. 4A to 4F show in vivo-derived designer EV characterization. FIG. 4A is a schematic representation of tissue nanotransfection (TNT) of skin in vivo and subsequent isolation of designer EVs. FIG. 4B shows particle concentration in the order of ten trillion EVs per $cm^2$ of skin. FIG. 4C shows average particle size in the range of 109-135 nm. FIG. 4D shows both sham and miR-146a designer EVs presented positive expression of the membrane EV marker tetraspanin CD9. FIG. 4E shows qRT-PCR characterization of these in vivo-derived miR-146A designer EVs showing successful loading of the molecular cargo. FIGS. 4F and 4G shows in vivo production of labeled designer EVs, where 24 hours after TNT of the skin with a plasmid encoding for CD63-GFP (EV tracer), GFP-labeled designer EVs are clearly being produced by the transfected skin cells (white arrows) compared to control tissue (FIG. 4G) from non-transfected animals.

FIGS. 5A to 5F show in vivo-derived designer EVs modulate inflammation in the lung. Effect of miR-146a designer EVs after 4 hours of treatment during ventilation, showing improved physiological parameters (FIGS. 5A to 5D), a significant decrease in BAL protein content (FIG. 5E), and a decreasing trend in the secretion of inflammatory cytokines (FIG. 5F, *p-value=0.022).

FIG. 6A shows in vivo imaging of organs collected from an animal treated for 24 hours with designer EVs functionalized with CD200 ligand to target alveolar macrophages. FIG. 6B shows IF images of lung tissue 24 hours after treatment with fluorescently labeled functionalized designer EVs showing successful uptake and by lung cells (arrows).

DETAILED DESCRIPTION

Figure 1:
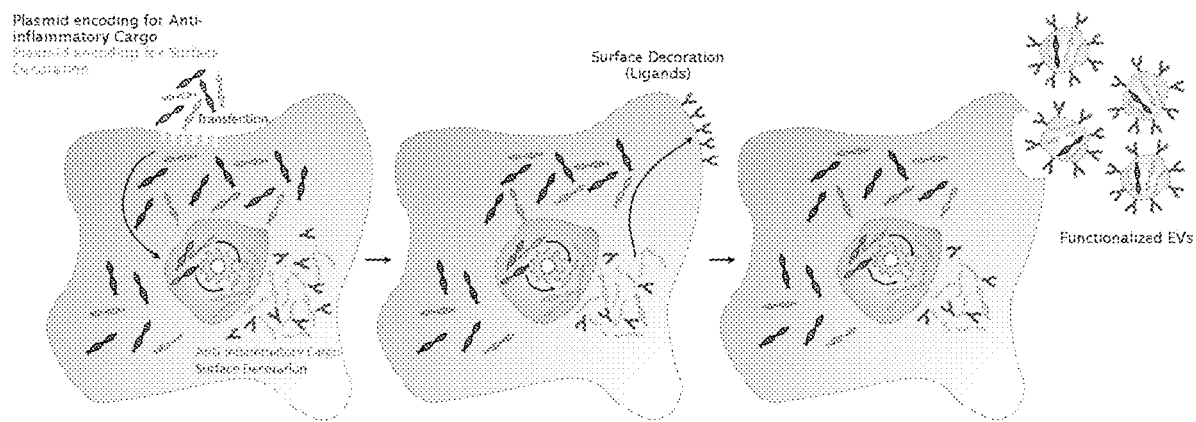
FIG. 1 is a schematic representation of production of custom-made nanocarriers loaded with anti-inflammatory cargo and/or decorated with cell-targeting ligands after transfection of cells or tissues.

Disclosed are lung-targeted extracellular vesicles (EVs) loaded with an anti-inflammatory cargo, as well as compositions, systems, and methods for making same. The disclosed EVs can contain a lung targeted ligand, such as a fusion protein containing a lung targeting moiety. Also disclosed is a composition comprising an EV containing the disclosed fusion protein. In some embodiments, the EV is loaded with an anti-inflammatory cargo. Also disclosed is an EV-producing cell engineered to produce the disclosed EVs. Also disclosed is a method for making the disclosed EVs that involves culturing the disclosed EV-producing cells under conditions suitable to produce EVs. The method can further involve purifying EVs from the cell.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

The disclosed EVs can in some embodiments be any that can be produced by a cell. Cells secrete extracellular vesicles (EVs) with a broad range of diameters and functions, including apoptotic bodies (1-5 μm), microvesicles (100-1000 nm in size), and vesicles of endosomal origin, known as exosomes (50-150 nm).

The disclosed extracellular vesicles may be prepared by methods known in the art. For example, the disclosed extracellular vesicles may be prepared by expressing in a eukaryotic cell an mRNA that encodes the cell-targeting ligand. In some embodiments, the cell also expresses an mRNA that encodes a anti-inflammatory cargo. The mRNA for the cell-targeting ligand and the anti-inflammatory cargo may be expressed from vectors that are transfected into suitable production cells for producing the disclosed EVs. The mRNA for the cell-targeting ligand and the anti-inflammatory cargo may be expressed from the same vector (e.g., where the vector expresses the mRNA for the cell-targeting ligand and the anti-inflammatory cargo from separate promoters), or the mRNA for the cell-targeting ligand and the anti-inflammatory cargo may be expressed from separate vectors. The vector or vectors for expressing the mRNA for the cell-targeting ligand and the anti-inflammatory cargo may be packaged in a kit designed for preparing the disclosed extracellular vesicles.

Also disclosed is a composition comprising an EV containing the disclosed targeting ligands. In some embodiments, the EV is loaded with a disclosed anti-inflammatory cargos. Also disclosed is an EV producing cell engineered to secrete the disclosed EVs.

EVs, such as exosomes, are produced by many different types of cells including immune cells such as B lymphocytes, T lymphocytes, dendritic cells (DCs) and most cells. EVs are also produced, for example, by glioma cells, platelets, reticulocytes, neurons, intestinal epithelial cells and tumor cells. EVs for use in the disclosed compositions and methods can be derived from any suitable cell, including the cells identified above. Non-limiting examples of suitable EV producing cells for mass production include dendritic cells (e.g., immature dendritic cell), Human Embryonic Kidney 293 (HEK) cells, 293T cells, Chinese hamster ovary (CHO) cells, and human ESC-derived mesenchymal stem cells. EVs can also be obtained from autologous patient-derived, heterologous haplotype-matched or heterologous stem cells so to reduce or avoid the generation of an immune response in a patient to whom the exosomes are delivered. Any EV-producing cell can be used for this purpose.

Also disclosed is a method for making the disclosed EVs loaded with an anti-inflammatory cargo that involves culturing the disclosed EV-producing cell engineered to secrete the disclosed EVs. The method can further involves purifying EVs from the cells.

EVs produced from cells can be collected from the culture medium by any suitable method. Typically a preparation of EVs can be prepared from cell culture or tissue supernatant by centrifugation, filtration or combinations of these methods. For example, EVs can be prepared by differential centrifugation, that is low speed (<20000 g) centrifugation to pellet larger particles followed by high speed (>100000 g) centrifugation to pellet EVs, size filtration with appropriate filters, gradient ultracentrifugation (for example, with sucrose gradient) or a combination of these methods.

The disclosed EVs can be targeted to the lung by expressing on the surface of the EVs a targeting moiety which binds to a cell surface moiety expressed on the surface of the lung cell. Examples of suitable targeting moieties are short peptides, scFv and complete proteins, so long as the targeting moiety can be expressed on the surface of the exosome. Peptide targeting moieties may typically be less than 100 amino acids in length, for example less than 50 amino acids in length, less than 30 amino acids in length, to a minimum length of 10, 5 or 3 amino acids.

In some embodiments, type II pneumocytes can be targeted using surfactant protein-A (SPA). EVs functionalized with SPA interact with receptor P63/CKAP4 on type II cells. In some embodiments, the targeting moiety is SPA1 having the amino acid sequence:

(SEQ ID NO: 1)
MWLCPLALNLILMAASGAVCEVKDVCVGTPGIPGECGEKGEPGERGPPGLP

AHLDEELQATLHDFRHQILQTRGALSLQGSIMTVGEKVFSSNGQSITFDAI

QEACARAGGRIAVPRNPEENEAIASFVKKYNTYAYVGLTEGPSPGDFRYSD

GTPVNYTNWYRGEPAGRGKEQCVEMYTDGQWNDRNCLYSRLTICEF, or a variant and/or fragment thereof having at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity to SEQ ID NO:1 that can interact with receptor P63/CKAP4 on type II cells.

In some embodiments, the targeting ligand is a fragment of SPA1 comprising at least 100, 110, 120, 130, 140, 141, 142, 143, 144, 145, 156, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, or 199 contiguous amino acids of SEQ ID NO:1 or a variant thereof.

In some embodiments, the targeting moiety is SPA2 having the amino acid sequence (SEQ ID NO: 2)
MWLCPLALTLILMAASGAACEVKDVCVGSPGIPGTPGSHGLPGRDGRDGVK

GDPGPPGPMGPPGETPCPPGNNGLPGAPGVPGERGEKGEAGERGPPGLPAH

LDEELQATLHDFRHQILQTRGALSLQGSIMTVGEKVFSSNGQSITFDAIQE

ACARAGGRIAVPRNPEENEAIASFVKKYNTYAYVGLTEGPSPGDFRYSDGT

PVNYTNWYRGEPAGRGKEQCVEMYTDGQWNDRNCLYSRLTICEF, or a variant and/or fragment thereof having at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity to SEQ ID NO:2 that can interact with receptor P63/CKAP4 on type II cells.

In some embodiments, the targeting ligand is a fragment of SPA2 comprising at least 100, 110, 120, 130, 140, 141, 142, 143, 144, 145, 156, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, or 248 contiguous amino acids of SEQ ID NO:2 or a variant thereof.

In some embodiments, lung macrophages can be targeted using membrane glycoprotein CD200. EVs functionalized with CD200 preferentially interact with the CD200R receptor in alveolar macrophages. In some embodiments, the targeting moiety is CD200 having the amino acid sequence:

(SEQ ID NO: 3)
MERLVIRMPFCHLSTYSLVWVMAAVVLCTAQVQVVTQDEREQLYTPASLKC

SLQNAQEALIVTWQKKKAVSPENMVTFSENHGVVIQPAYKDKINITQLGLQ

NSTITFWNITLEDEGCYMCLFNTFGFGKISGTACLTVYVQPIVSLHYKFSE

DHLNITCSATARPAPMVFWKVPRSGIENSTVTLSHPNGTTSVTSILHIKDP

KNQVGKEVICQVLHLGTVTDFKQTVNKGYWFSVPLLLSIVSLVILLVLISI

LLYWKRHRNQDREP, or a variant and/or fragment thereof having at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity to SEQ ID NO:3 that can interact with lung macrophages.

In some embodiments, the targeting ligand is a fragment of CD200 comprising at least 100, 110, 120, 130, 140, 141, 142, 143, 144, 145, 156, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, or 269 contiguous amino acids of SEQ ID NO:3 or a variant thereof.

The cell targeting ligand can in some cases be expressed on the surface of the EV by expressing it as a fusion protein with an exosomal or lysosomal transmembrane protein. A number of proteins are known to be associated with exosomes; that is they are incorporated into the exosome as it is formed. Examples include but are not limited to Lamp-1, Lamp-2, CD13, CD86, Flotillin, Syntaxin-3, CD2, CD36, CD40, CD40L, CD41a, CD44, CD45, ICAM-1, Integrin alpha4, LiCAM, LFA-1, Mac-1 alpha and beta, Vti-IA and B, CD3 epsilon and zeta, CD9, CD18, CD37, CD53, CD63, CD81, CD82, CXCR4, FcR, GluR2/3, HLA-DM (MHC II), immunoglobulins, MHC-I or MHC-II components, TCR beta and tetraspanins.

The disclosed extracellular vesicles further may be loaded an anti-inflammatory agent, where the extracellular vesicles deliver the agent to a target cell. Suitable anti-inflammatory agents include but are not limited to therapeutic drugs (e.g., small molecule drugs), therapeutic proteins, and therapeutic nucleic acids (e.g., therapeutic RNA). In some embodiments, the disclosed extracellular vesicles comprise a therapeutic RNA (also referred to herein as a "cargo RNA"). For example, in some embodiments the fusion protein containing the cell-targeting motif also includes an RNA-domain (e.g., at a cytosolic C-terminus of the fusion protein) that binds to one or more RNA-motifs present in the cargo RNA in order to package the cargo RNA into the extracellular vesicle, prior to the extracellular vesicles being secreted from a cell. As such, the fusion protein may function as both of a "cell-targeting protein" and a "packaging protein." In some embodiments, the packaging protein may be referred to as extracellular vesicle-loading protein or "EV-loading protein."

In some embodiments, the cargo RNA is an miRNA, shRNA, mRNA, ncRNA, sgRNA or any combination thereof. For example, in some embodiments, the anti-inflammatory agent is micro-RNA 146a.

Additional anti-inflammatory microRNAs that could be used include miR-155, miR-9, miR-210, miR-146b, and miR-181. Anti-inflammatory miRs-155, miR-9, miR-210 and miR-146b have been shown to be upregulated during ALI/ARDS using murine models of high tidal volume ventilation and other pathological conditions such as acute lung injury (ALI), ventilator-induced lung injury (VILI), and osteoarthritis. MiR-181, on the other hand, modulates the inflammatory response in macrophages via IL-1α. MiR-9, miR-511, miR-146a, miR-23b and miR-181a, have been previously reported as anti-inflammatory miRNAs upregulated in the lung during sepsis and ARDS, specifically.

Designer EVs can also be used to efficiently deliver key grow factors, regulatory proteins, and anti-inflammatory cytokines to reduce lung inflammation and injury, and to enhance tissue repair during ARDS/VILI. The can be for examples be loaded with anti-inflammatory cytokines interleukin-10 and interleukin-4, regulatory protein secreted leukocyte protease inhibitor (SLPI), and keratinocyte growth factor (KGF), which have shown to reduce mortality and modulate inflammation during ARDS.

The cargo RNA of the disclosed extracellular vesicles may be of any suitable length. For example, in some embodiments the cargo RNA may have a nucleotide length of at least about 10 nt, 20 nt, 30 nt, 40 nt, 50 nt, 100 nt, 200 nt, 500 nt, 1000 nt, 2000 nt, 5000 nt, or longer. In other embodiments, the cargo RNA may have a nucleotide length of no more than about 5000 nt, 2000 nt, 1000 nt, 500 nt, 200 nt, 100 nt, 50 nt, 40 nt, 30 nt, 20 nt, or 10 nt. In even further embodiments, the cargo RNA may have a nucleotide length within a range of these contemplated nucleotide lengths, for example, a nucleotide length between a range of about 10 nt-5000 nt, or other ranges. The cargo RNA of the disclosed extracellular vesicles may be relatively long, for example, where the cargo RNA comprises an mRNA or another relatively long RNA.

Figure 2:
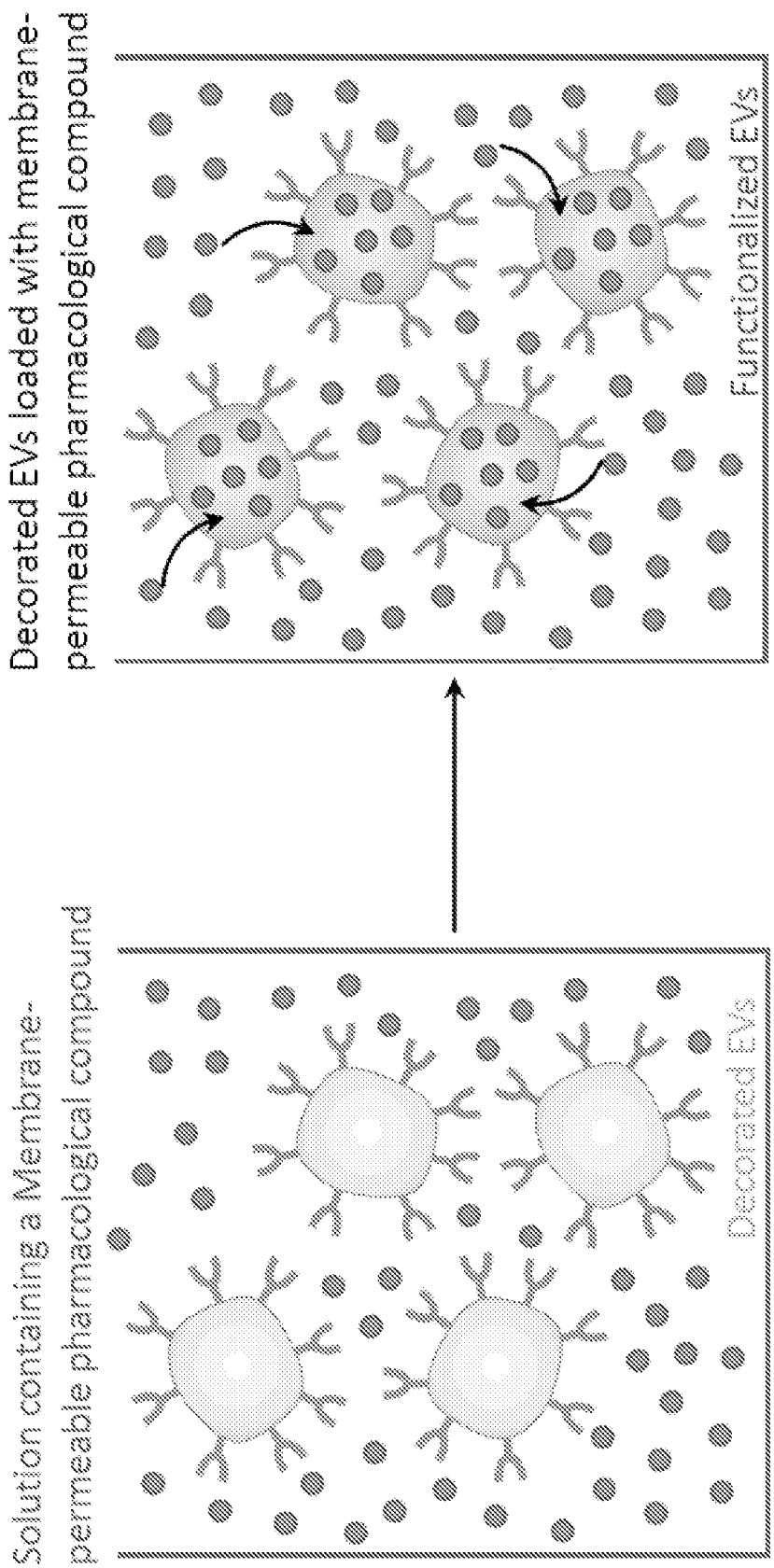
FIG. 2 is a schematic representation of surface-decorated EVs loaded with other anti-inflammatory cargo, for example, a membrane-permeable pharmacological compound.

In some embodiments, the anti-inflammatory cargo is a membrane-permeable pharmacological compound that is loaded into the EV after it is secreted by the cell. For example, in some embodiments, the anti-inflammatory cargo comprises the Y-27632 Rho-inhibitor (Calbiochem), which can diffuse into the EVs via a concentration gradient (see FIG. 2).

The disclosed method can be applied to load EVs with clinically relevant lipophilic compounds and other anti-inflammatory membrane permeable compounds. One example of this type of compounds are statins, more specifically Simvastatin which is used in clinical settings to reduce cholesterol levels in the blood. Simvastatin can be effectively delivered locally to the inflamed lung via designer EVs to dampen inflammation and aid faster recovery for patients with ALI/ARDS or VILI for example.

In some embodiments, the anti-inflammatory cargo is loaded into the EVs by diffusion via a concentration gradient.

Also contemplated herein are methods for using the disclosed EVs. For example, the disclosed extracellular vesicles may be used for delivering the disclosed anti-inflammatory cargo to a target lung cell, where the methods include contacting the target cell with the disclosed EVs. Therefore, also disclosed herein is a method of treating a lung disease in a subject, that involves administering to the subject a therapeutically effective amount of a composition containing cargo-loaded lung-targeted EVs disclosed herein. In some embodiments, the subject has ARDS.

The disclosed designer EVs can be used to modulate an extensive variety of inflammatory conditions, not only in the lung but in different organ systems basically by tailoring the ligands used to decorate the EVs. Additional pulmonary applications may include ventilator-induced lung injury (VILI), pulmonary fibrosis, and infectious diseases such as sepsis, flu, and pneumonia.

The disclosed EVs may be formulated as part of a pharmaceutical composition for treating a disease or disorder of the lung and the pharmaceutical composition may be administered to a patient in need thereof to deliver the cargo to target lung cells in order to treat the lung disease or disorder.

The disclosed EVs may be administered to a subject by any suitable means. Administration to a human or animal subject may be selected from parenteral, intramuscular, intracerebral, intravascular, subcutaneous, or transdermal administration. Typically the method of delivery is by injection. Preferably the injection is intramuscular or intravascular (e.g. intravenous). A physician will be able to determine the required route of administration for each particular patient.

The EVs are preferably delivered as a composition. The composition may be formulated for parenteral, intramuscular, intracerebral, intravascular (including intravenous), subcutaneous, or transdermal administration. Compositions for parenteral administration may include sterile aqueous solutions which may also contain buffers, diluents and other suitable additives. The EVs may be formulated in a pharmaceutical composition, which may include pharmaceutically acceptable carriers, thickeners, diluents, buffers, preservatives, and other pharmaceutically acceptable carriers or excipients and the like in addition to the EVs.

Parenteral administration is generally characterized by injection, such as subcutaneously, intramuscularly, or intravenously. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof. Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include sodium chloride injection, ringers injection, isotonic dextrose injection, sterile water injection, dextrose and lactated ringers injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone.

Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles; and sodium hydroxide, hydrochloric acid, citric acid or lactic acid for pH adjustment. The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations can be packaged in an ampoule, a vial or a syringe with a needle. All preparations for parenteral administration should be sterile, as is known and practiced in the art.

A therapeutically effective amount of composition is administered. The dose may be determined according to various parameters, especially according to the severity of the condition, age, and weight of the patient to be treated; the route of administration; and the required regimen. A physician will be able to determine the required route of administration and dosage for any particular patient. Optimum dosages may vary depending on the relative potency of individual constructs, and can generally be estimated based on EC50s found to be effective in vitro and in vivo animal models. In general, dosage is from 0.01 mg/kg to 100 mg per kg of body weight. A typical daily dose is from about 0.1 to 50 mg per kg, preferably from about 0.1 mg/kg to 10 mg/kg of body weight, according to the potency of the specific construct, the age, weight and condition of the subject to be treated, the severity of the disease and the frequency and route of administration. Different dosages of the construct may be administered depending on whether administration is by intramuscular injection or systemic (intravenous or subcutaneous) injection.

Preferably, the dose of a single intramuscular injection is in the range of about 5 to 20 µg. Preferably, the dose of single or multiple systemic injections is in the range of 10 to 100 mg/kg of body weight.

Due to construct clearance (and breakdown of any targeted molecule), the patient may have to be treated repeatedly, for example once or more daily, weekly, monthly or yearly. Persons of ordinary skill in the art can easily estimate repetition rates for dosing based on measured residence times and concentrations of the construct in bodily fluids or tissues. Following successful treatment, it may be desirable to have the patient undergo maintenance therapy, wherein the construct is administered in maintenance doses, ranging from 0.01 mg/kg to 100 mg per kg of body weight, once or more daily, to once every 20 years.

A number of embodiments of the invention have been described. Nevertheless, it will be understood that various modifications may be made without departing from the spirit and scope of the invention. Accordingly, other embodiments are within the scope of the following claims.

EXAMPLES

Example 1

FIG. 3 shows in vivo-derived designer EVs characterization and delivery. FIG. 3A is a bar graph showing miR-146a and SH-loaded EVs characterization via qRT-PCR. SH-CT or miR-loaded EVs were delivered before ventilation via intubation-mediated intratracheal delivery. FIG. 3B is a bar graph showing physiology measurements from animals treated with SH-CT or miR-146A-loaded EVs (MV protocol: tidal volume of 12 cc/kg, respiratory rate of 150 breaths/min, at 0 cm H2O positive end-expiratory pressure for 4 hours). FIG. 3C contains bar graphs showing changes in BAL protein content for SH and mir-146a treated animals after 4h of MV. FIG. 3D is a bar graph showing average size distribution for EVs loaded with mock plasmid (sham control—SH) or anti-inflammatory miR-146a.

In-vivo derived designer EVs loaded with anti-inflammatory miR-146a were obtained by nanotransfecting the dorsal skin of C57BL6 mice (8-10 weeks old) with plasmids encoding for miR-146a (OriGene). 24 hours after skin transfection, the loaded-EVs were collected from skin biopsies and isolated using an ExoQuick kit (System Bio). After isolation the EVs were kept in pellet form and then suspended in a 0.9% sodium chloride solution for subsequent use. EVs loading efficiency was measured by quantifying miR-146a copy numbers via qRT-PCR.

Designer EVs were evaluated in vivo. Briefly, mechanical ventilation (MV) was conducted following a previously reported ventilation protocol which will induce significant lung injury, with a tidal volume of 12 cc/kg, respiratory rate of 120 breaths/min, at 0 cm $H_2O$ positive end-expiratory pressure for 4 hours. For these experiments designer EVs were delivered into the lungs of these mice via intratracheal injection (using 2 µL/g mouse weight) prior to MV. Lung physiology and oxygen saturation data will be collected during the ventilation procedure. After 4 hours the animals were euthanized and bronchoalveolar lavage (BAL) and tissue was collected.

Example 2: In Vitro Approaches Towards Manufacturing Designer EVs

Figures 3A, 3B, 3C:
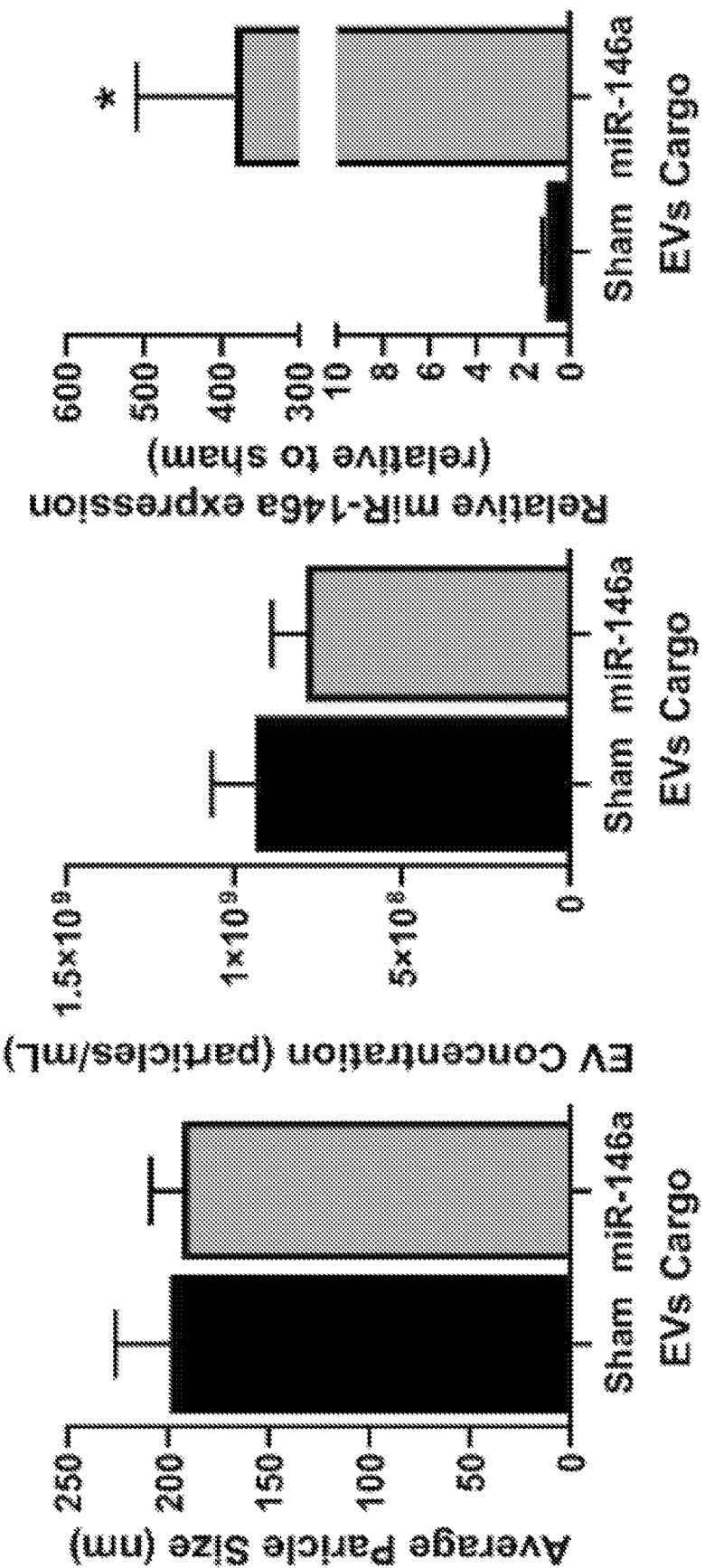
FIGS. 3A to 3E show in vitro-derived designer EV characterization.
Figure 3D:
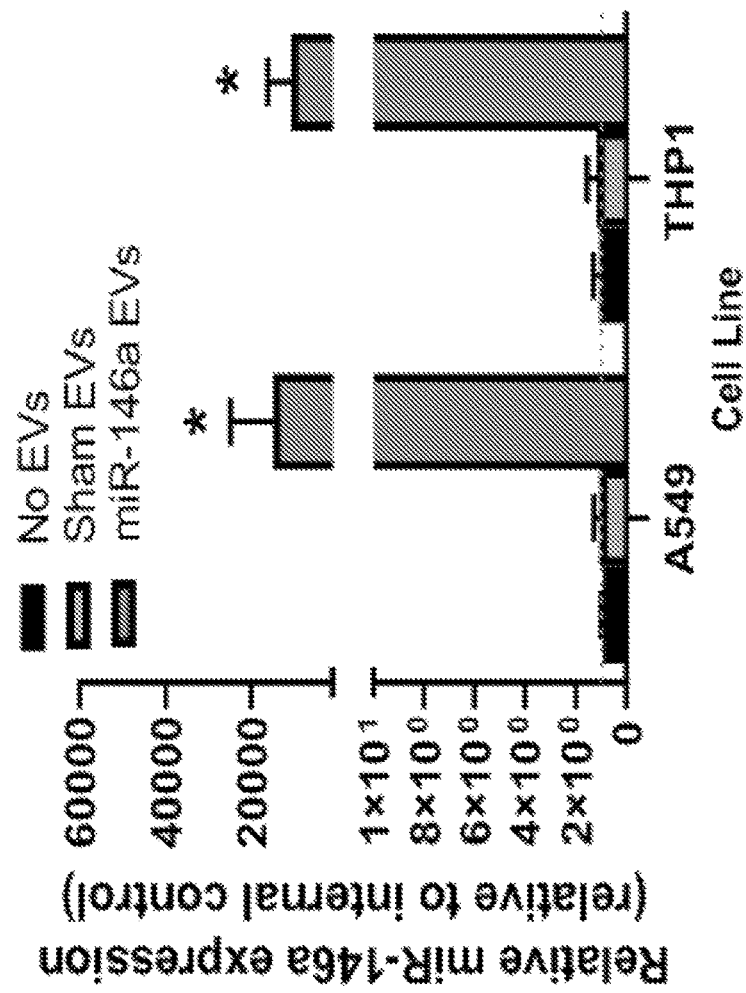
Figure 3E:
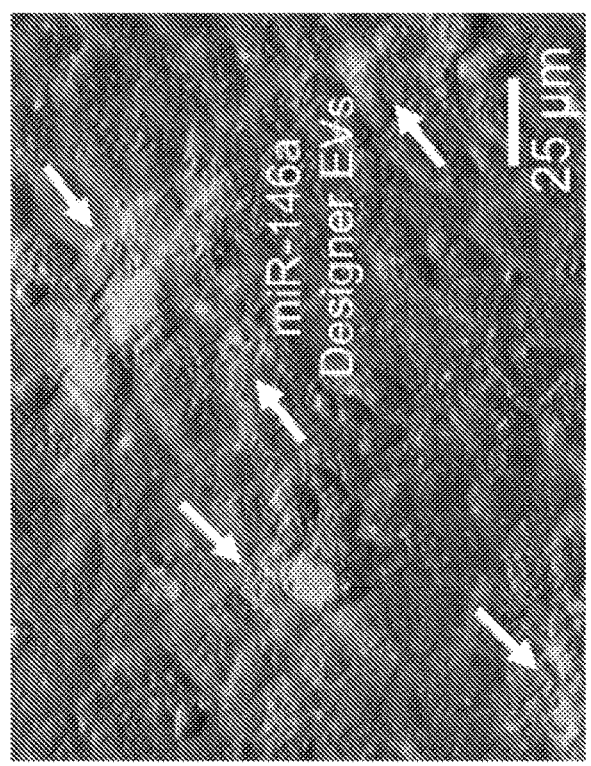
Figures 3F, 3G:
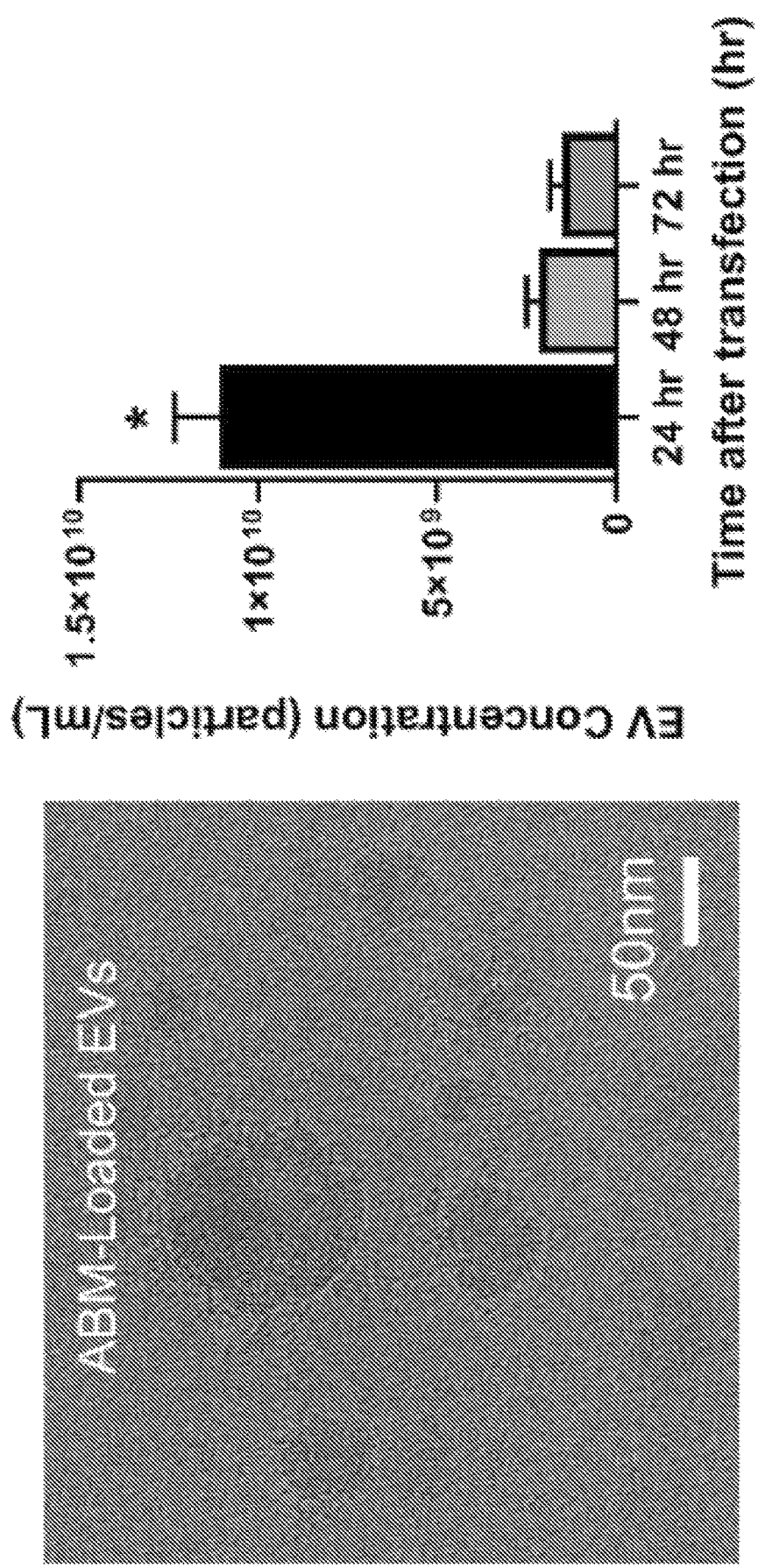
Figure 3H:
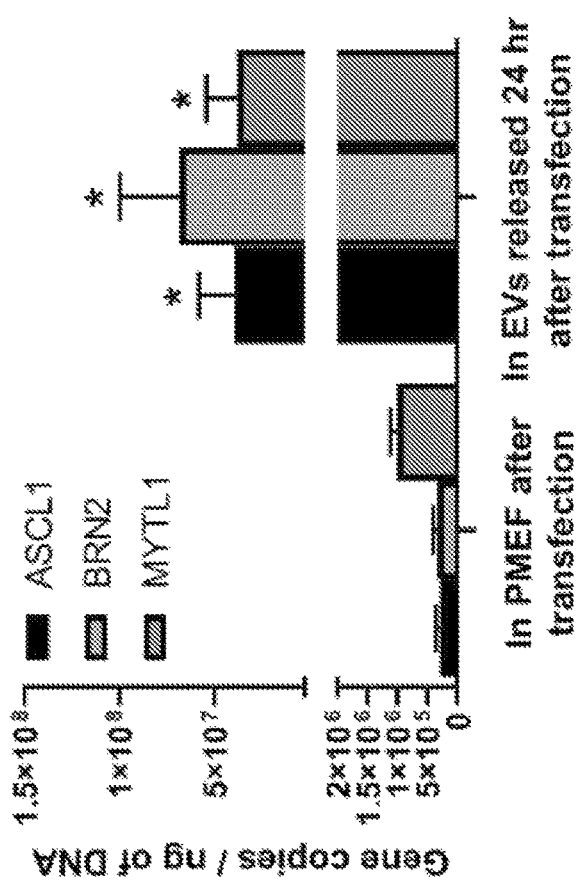
Figure 3I:
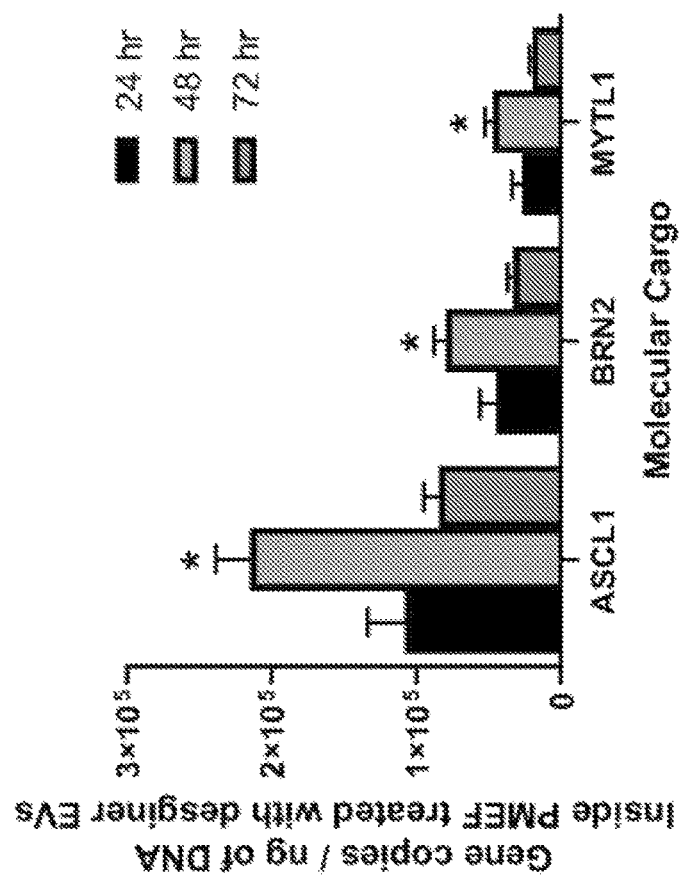
Figure 5A:
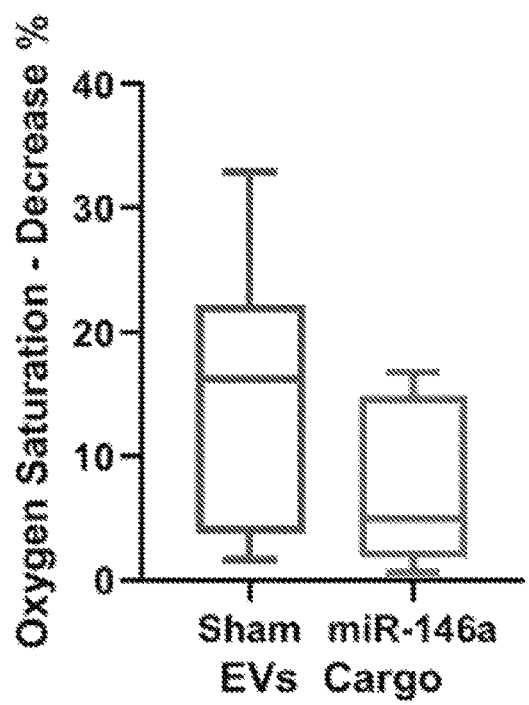
Figure 5B:
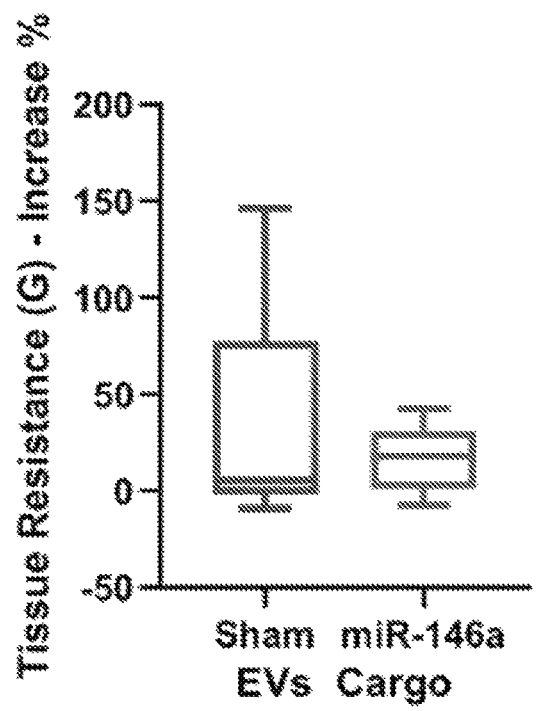
Figure 5C:
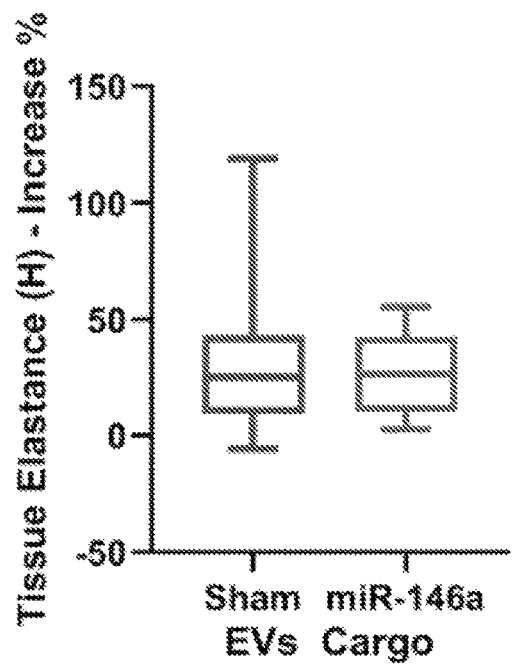
Figure 5D:
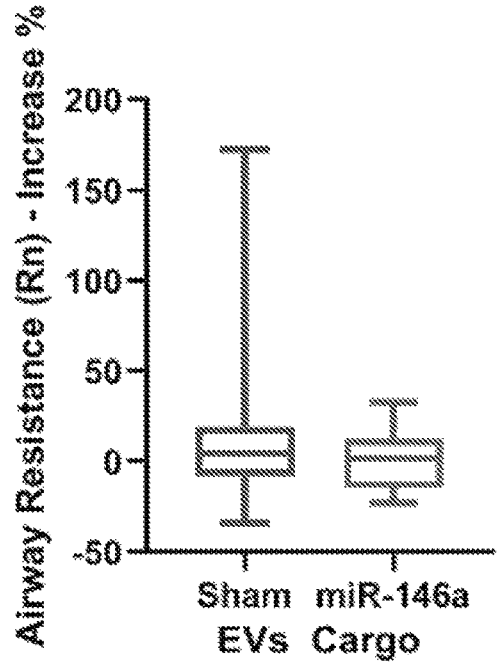

Nanochannel-based electroporation was used to controllably overexpress cargo of interest within donor cells and customize the content and surface decoration of the EVs. Nanochannel-based electroporation can yield transfection efficiencies and cell viabilities ~100%, and is not limited by capsid size constraints. This approach was used to obtain designer EVs loaded with anti-inflammatory miR-146A from multiple cell sources, including primary cultures of mouse dendritic cells and embryonic fibroblasts, as well as human cell lines (FIG. 3A-3E). Characterization of the EV content showed successful incorporation of the molecular cargo of interest (FIG. 3C) compared to the sham-loaded EVs. Such EVs were then effectively used to modulate gene expression in cultures of human lung epithelial cells and human macrophages (FIG. 3D). Designer EVs loaded with pro-neural factor genes ASCL1, BRN2, and MYT1L (ABM) were also obtained from primary cultures of mouse fibroblasts. Studies of the dynamics of ABM-loaded designer EV release and uptake revealed that EV release from donor cells peaks 24 hours post-transfection, with a concentration in the order of billions of particles/ml. The number of gene copies packed inside the EVs exceeded the original number of copies delivered to the "donor" cells by approximately 3 orders of magnitude, suggesting intracellular amplification of the therapeutic cargo prior to EV release.

Example 3: In Vivo Approaches Towards Manufacturing Designer EVs

Nanochannel-based tissue transfection for the derivation of designer EVs from in vivo tissues could conceivably enable the use of the patient's own tissue as a prolific EV bioreactor, which could have major clinical and translational implications. This method had a yield of around ten trillion EVs loaded with anti-inflammatory miR-146A from approximately 1 cm² of mouse skin (FIG. 4). Such EVs were then effectively used to stem inflammation caused by mechanical ventilation (FIG. 5).

Example 3

ARDS represents a significant burden to the health care system, considering the need for critical care, prolonged hospitalization times, and slow recovery. According to the American Lung Association (2013) there are approximately 190,000 cases of ARDS annually in the United States. The mortality rate for patients with ARDS is high, ranging between 38-45%. ARDS is normally caused by an underlying condition such as blunt trauma to the lung or sepsis. In the context of lung injury, sepsis is a life threatening condition, characterized by a severe systemic inflammatory response caused by infection, and it is the major cause of death for ICU patients. The hallmarks of ARDS include severe hypoxia, alveolar-capillary barrier dysfunction, flooding of small airways with reduced production of pulmonary surfactant, and activation of pro-inflammatory pathways. While mechanical ventilation is used to support oxygen therapy, the mechanical stresses exacerbate the initial injury and can cause ventilator-induced lung injury (VILI), which has an even higher mortality rate. All these factors further worsen the underlying lung injury, thus fueling a positive feedback loop that favors inflammation and could lead to multisystem organ failure, and death. While there is currently no cure for ARDS, the use of anti-inflammatory approaches targeting the lung have shown significant promise. Cell-based therapies (e.g. endothelial progenitors, mesenchymal stem cells), for example, have been shown to reduce inflammation and enhance lung repair via trophic and anti-inflammatory/infection mechanisms. However, significant concerns still remain about the safety of progenitor-based cell therapies, including the potential for tumorigenesis and high immunogenic responses, stemming in part from excessive ex vivo processing. While specific therapeutic agents have been identified, efficient delivery of therapeutics to inflamed lungs remains a major challenge in critically ill patients. To overcome these limitations, key anti-inflammatory and anti-bacterial molecular cargo is efficiently and selectively delivered using functionalized designer EVs to reduce lung inflammation and injury, and to enhance tissue repair during sepsis-induced ARDS. Designer EVs loaded with the molecular cargo described in Table 1 are engineered.

TABLE 1

Molecular cargo for designer EVs to target sepsis-induced ARDS.

| Goal | Plasmids | Rationale |
| --- | --- | --- |
| Designer EVs loaded with specific cargo associated with the success of progenitor-based cell therapies. | Interleukins 4 and 10 (IL4, 10) Secreted leukocyte protease inhibitor (SLPI) Keratinocyte growth factor (KGF) | These factors have been shown to have antiinflammatory (IL4, 10), regulatory (SLPI), and trophic (KGF) properties that reduce inflammation and mortality associated with ARDS. |
| Designer EVs with antibacterial properties. | Cathelicidin (CAMP) | Known to permeate the membranes of pathogens. It may reduce immune response to endotoxin lipopolysaccharide (LPS) by hindering LPS-binding to the endotoxin receptor CD14 in immune cells. |

Protocols have been optimized to obtain designer EVs derived from living tissues. For this focus area, in vivo-derived designer EVs loaded with the anti-inflammatory or anti-microbial cargo described in Table 1 are obtained by nanotransfecting the skin of 8-10 week old C57BL6 mice, in vivo, with plasmids encoding for each factor. Tissue nanotransfection platforms are fabricated in a cleanroom using a combination of projection and contact photolithography, and deep reactive ion etching, as previously reported. EVs will be collected from skin biopsies at different time points post-transfection. For EV isolation, skin samples are dissociated and homogenized using a gentleMACS dissociator. EVs are selectively precipitated using a total exosome isolation kit and stored at −80° C. for later use.

Figures 6A, 6B:
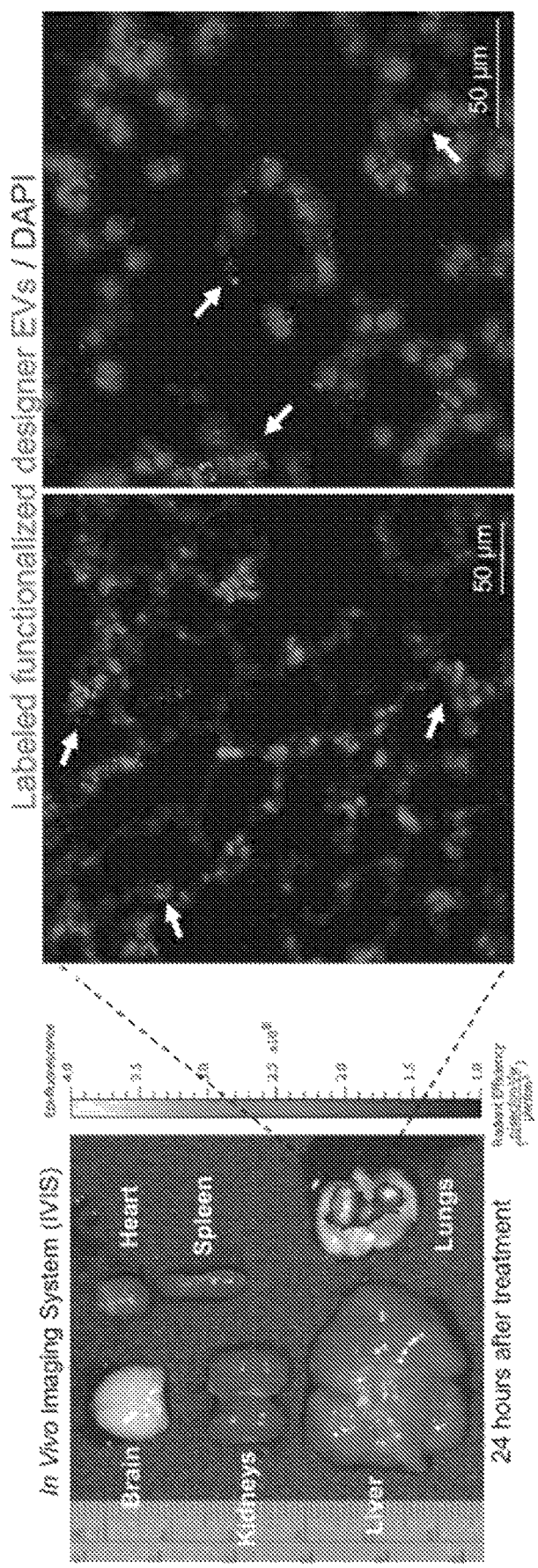
FIGS. 6A and 6B show functionalized designer EVs to target the inflamed lung. Designer EVs can be functionalized to target different cellular compartments at the alveolar space.

Designer EVs are functionalized for targeted delivery to lung epithelium and macrophages as these cellular compartments are a significant source of inflammation during ARDS. Functionalized designer EVs are obtained via nanotransfection with plasmids for surfactant protein-A (SPA) and membrane glycoprotein CD200 (FIG. 6). SPA-functionalized EVs are expected to interact with receptor P63/CKAP4 on alveolar pneumocytes and have the potential to also bind to the Toll-like Receptor-2 (TLR2) in these cells, damping the activation of the NFκβ inflammatory pathway. CD200-functionalized EVs will likely preferentially interact with the CD200R receptor in alveolar macrophages to regulate their pro-inflammatory state. Additional ligands targeting endothelium will be used in combination with SPA and CD200 for designer EVs delivered through systemic circulation to favor interaction with the pulmonary microvasculature. EVs co-functionalized with SDF1 ligands will preferentially interact with the CXCR7 receptor in lung's vasculature, which is upregulated under injury conditions, likely facilitating anchoring of designer EVs to the lung vasculature for subsequent translocation into the alveolar space. Identifying the best administration route for designer EVs is also an important component of optimizing designer EVs for therapeutic applications. As such, three non-invasive administration routes (Table 2) are compared to define the best delivery method for therapeutic applications.

TABLE 2

Delivery routes used to administer designer EVs.

| Delivery Route | Approach |
| --- | --- |
| Nasal delivery | A concentrated bolus of functionalized designer EVs will be administered through the nostrils of the animals (2 µL/g). |
| Systemic bolus delivery | Intravenous injection, where two or more boluses of designer EVs will be administered through a tail vein injection. |
| Systemic cumulative delivery from skin | The designer EVs will be allowed to percolate (and gradually accumulate) into the circulation from the transfected skin (i.e. EVs will not be purified from a skin biopsy for bolus-type delivery). |

A dose sensitivity analysis is run on healthy and diseased animals (Table 3), treated with functionalized and non-functionalized anti-inflammatory, anti-bacterial, or sham-loaded designer EVs for each delivery method. For this analysis bronchoalveolar lavage (BAL), blood, and lungs are collected and the relative expression of genes encoding for the molecular cargo delivered, as well as key pro- and anti-inflammatory factors (Table 4), are quantified via qRT-PCR. This analysis defines the optimal dose concentration to achieve significant modulation of lung inflammation in vivo. These results are correlated with the area of the transfected skin required to obtain the optimal concentration of designer EVs. Off-target accumulation and clearance are tested via quantitative biodistribution studies (FIG. 6).

TABLE 3

Experimental groups used for in vivo evaluation (for both injury models).

| Injury model | Treatment |
| --- | --- |
| Healthy animal | Functionalized antiinflammatory, anti-microbial or sham designer EVs |
| Sepsis-induced ARDS | Non-functionalized antiinflammatory, anti-microbial or sham designer EVs |
| Two-hit model (Sepsis-induced ARDS and MV) | No treatment |

TABLE 4

Pro/anti-inflammatory panel

Pro-inflammatory panel

Interferon-gamma (IFN-γ)
Tumor necrosis factor-alpha (TNFα)
Interleukin-1 β (IL-1β)
Interleukin-2 (IL-2)
KC (analog for Interleukin-8 in humans)

TABLE 4-continued

Pro/anti-inflammatory panel

RANTES (Chemokine (C-C motif) ligand 5)
HMGB1 (High mobility group box 1 protein)
Interleukin-6 (IL-6) - pro-inflammatory or anti-inflammatory TH2 cytokine
Anti-inflammatory panel Interleukin-4 (IL-4)
Interleukin-10 (IL-10)

In addition to in vivo studies, extensive in vitro characterization of the EVs is conducted to better understand their nature. This includes analyses of size distribution, charge and particle concentration as a function of cargo and surface decoration using a Nanosight and a Zeta potential analyzer system. EV loading efficiency is defined by quantifying copy numbers for each gene packed per EV using an Absolute Quantification qRT-PCR protocol with a standard curve generated for each plasmid DNA. These results are correlated with the copy number transfected into the skin. Total RNA-seq is used to characterize the content of designer EVs loaded with anti-inflammatory, anti-microbial, or sham molecular cargo to obtain an in-depth record of the coding and noncoding RNA forms packed inside designer EVs. Additionally, comparative proteomic analyses (at the membrane and cytosolic levels) of functionalized and non-functionalized designer EVs is conducted to further define the efficiency of anti-inflammatory and anti-bacterial molecular cargo packing, as well as membrane ligand expression.

To better understand the action mechanism of designer EVs, in vivo performance studies in murine models of lung injury (Table 3) are benchmarked to well-established in vitro models of injury (Table 5). In vitro models enable a systematic study of the effect of designer EVs on specific cell populations, while the in vivo ones will provide a better understanding of the response under more pathophysiological conditions, where the interplay between multiple organ systems is vital. In vivo, the efficacy of designer EVs to reduce inflammation and bacterial infection is assessed using a mouse model of sepsis-induced ARDS and a two-hit model. These models help determine the potential effect of the level of inflammation attenuation observed with specific concentrations of designer EVs under infection. In vitro models of barotrauma and volutrauma are used to probe designer EVs on isolated cellular components of lung tissue and bacterial cultures.

TABLE 5

Experimental groups used for in vitro evaluation (for both injury models).

| Injury model | Treatment |
| --- | --- |
| No injury | Pre-treatment for 24 hours with anti-inflammatory or Sham designer EVs |
| Barotrauma | Concomitant-treatment for 24 hours with anti-inflammatory or Sham designer EVs |
| Volutrauma | No treatment |

For in vivo injury models designer EVs are administered (Table 2) at various doses (e.g. single vs. repeated) and timepoints (e.g. pre- vs. postinjury). To model sepsis-induced ARDS, 8-10 week old C57BL6 mice are subject to cecal ligation and puncture (CLP) or sham laparotomy. Pulmonary edema is evaluated after CLP via ultrasound imaging using a Vevo 2100 system. Animals are sacrificed and BAL, blood, and major organs (i.e. lungs, heart, spleen, liver and kidneys) are collected after perfusion with sterile saline for downstream analysis. Using the two-hit model enables replication of more clinically relevant conditions, where patients would require mechanical ventilation due an underlying infection. For this model, 8-10 week old C57BL6 mice are initially subject to CLP or sham laparotomy, and 24 hours after CLP the animals are mechanically ventilated with an injurious protocol (tidal volume of 12 cc/kg, at 120 breaths/min, and 0 cm $H_2O$ positive end-expiratory pressure) for 4 hours using a FlexiVent FX, SCI REQ. Lung physiology and oxygen saturation data are collected during the MV procedure, the animals are sacrificed by anesthetic overdose at the end of the MV, and BAL, blood, and major organs are collected after perfusion with sterile saline for downstream analysis. The cellular content of BAL samples is characterized via inflammatory cell counts (i.e. alveolar macrophages, lymphocytes, eosinophils, neutrophils, and mast cells). BAL protein content is also evaluated, as elevated protein content correlates with loss of integrity of the alveolar-capillary barrier function. After protein quantification all BAL and plasma samples will be screened for expression of pro- and anti-inflammatory cytokines and factors (Table 4) using custom-made cytokine arrays. The relative expression of the molecular cargo delivered in vivo (for the therapies described in Table 1) and their effect on the expression of key anti- and pro-inflammatory molecular markers (described in Table 4) is assessed via qRT-PCR.

For in vitro injury models, co-cultures of primary lung epithelial cells and macrophages derived from mice are exposed to barotrauma or volutrauma injury. Barotrauma injury is induced using a previously published cyclic pressure model. For this, the cells are co-cultured on transwell inserts and the apical compartment is pressurized for 24 hours to achieve a cyclic oscillatory pressure between 0 to 20 $cmH_2O$ at a frequency of 0.2 Hz, to simulate pressure magnitudes similar to those in mechanical ventilation and a normal breathing frequency. Volutrauma injury will be simulated using a Flexcell FX-5000 Tension System. For this model, the cells will be co-cultured on modified 6 well plates with an elastomeric bottom and exposed to continuous cyclic stretching using an elongation of 10-20% at 1.25 Hz for 24 hours in a cell culture incubator. Secretion of key pro-inflammatory molecules (Table 4) into the media is monitored. ZO-1 is stained and imaged via IF to assess tight junction formation and maintenance, as an indicator of epithelial-endothelial barrier function after volutrauma injury. The experimental groups used for this evaluation are described in Table 5.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. An extracellular vesicle for treating Acute Respiratory Distress Syndrome (ARDS) produced by a method comprising:
   i) nanotransfecting skin cells with a non-viral vector encoding a fusion protein comprising:
      a) surfactant protein-A (SPA) capable of binding P63/CKAP4 or CD200 capable of binding CD200R and
      b) a heterologous exosomal or lysosomal transmembrane protein under conditions suitable for extracellular vesicle secretion, and
   ii) collecting the extracellular vesicles produced by the skin cells comprising the fusion protein, and wherein the extracellular vesicles are loaded with a therapeutic cargo, the heterologous exosomal protein or lysosomal transmembrane protein is inserted into the EV membrane and the SPA or CD200 protein are capable of binding P63/CKAP4 or CD200R.

2. The extracellular vesicle of claim 1, wherein the therapeutic cargo comprises miR146a.

3. The extracellular vesicle of claim 1, wherein the therapeutic cargo comprises Y-27632.

4. A method of treating Acute Respiratory Distress Syndrome (ARDS) in a subject, comprising administering to the subject a therapeutically effective amount of the extracellular vesicle of claim 1.

* * * * *